(12) United States Patent
Osaki et al.

(10) Patent No.: US 8,655,426 B2
(45) Date of Patent: Feb. 18, 2014

(54) DEVICE FOR MEASURING CONCENTRATION OF CONSTITUENT IN BLOOD AND MEASURING METHOD

(75) Inventors: Rie Osaki, Anjo (JP); Yasuyuki Haseo, Nishio (JP); Takashi Komura, Toyota (JP); Katsuyoshi Nishii, Okazaki (JP); Hirohiko Tatsumoto, Kariya (JP)

(73) Assignees: DENSO CORPORATION, Kariya (JP); Nippon Soken, Inc., Nishio (JP)

( * ) Notice: Subject to any disclaimer, the term of this patent is extended or adjusted under 35 U.S.C. 154(b) by 1040 days.

(21) Appl. No.: 12/385,901

(22) Filed: Apr. 23, 2009

(65) Prior Publication Data

US 2009/0270701 A1    Oct. 29, 2009

(30) Foreign Application Priority Data

Apr. 25, 2008    (JP) .................................. 2008-115337

(51) Int. Cl.
*A61B 5/00*    (2006.01)

(52) U.S. Cl.
USPC .......................................... 600/322; 600/344

(58) Field of Classification Search
USPC .................... 600/310–344, 473, 475–478
See application file for complete search history.

(56) References Cited

U.S. PATENT DOCUMENTS

| | | | | |
|---|---|---|---|---|
| 4,167,331 | A * | 9/1979 | Nielsen | 356/39 |
| 4,759,369 | A * | 7/1988 | Taylor | 600/323 |
| 4,796,636 | A | 1/1989 | Branstetter et al. | |
| 5,137,023 | A | 8/1992 | Mendelson et al. | |
| 5,178,142 | A * | 1/1993 | Harjunmaa et al. | 600/310 |
| 5,183,042 | A | 2/1993 | Harjunmaa et al. | |
| 5,313,941 | A | 5/1994 | Braig et al. | |
| 5,429,128 | A * | 7/1995 | Cadell et al. | 600/310 |
| 5,553,613 | A * | 9/1996 | Parker | 600/316 |
| 5,830,149 | A | 11/1998 | Oka et al. | |
| 6,172,743 | B1 | 1/2001 | Kley et al. | |
| 7,598,483 | B2 * | 10/2009 | Uchida | 250/216 |
| 2007/0177771 | A1 | 8/2007 | Tanaka et al. | |
| 2008/0081973 | A1* | 4/2008 | Hoarau | 600/336 |

FOREIGN PATENT DOCUMENTS

| | | |
|---|---|---|
| JP | A-05-176917 | 7/1993 |
| JP | A-11-64218 | 3/1999 |
| JP | A-2001-25462 | 1/2001 |
| JP | A-2004-251673 | 9/2004 |
| JP | A-2006-212161 | 8/2006 |

OTHER PUBLICATIONS

Office Action dated Sep. 9, 2009 from the Sweden Patent Office for corresponding patent application No. 0900552-1 (English translation enclosed).
Office Action mailed Feb. 16, 2010 from Japan Patent Office in corresponding JP Application No. 2008-115337 (and English translation).

* cited by examiner

*Primary Examiner* — Max Hindenburg
*Assistant Examiner* — John Pani
(74) *Attorney, Agent, or Firm* — Posz Law Group, PLC

(57) ABSTRACT

A device for measuring concentration of a constituent in blood includes: an irradiation unit for irradiating light toward a living body, the light having a wavelength disposed in a light absorption band of the constituent in the blood; a light receiving unit for receiving light, which is reflected in the living body or transmitted through the living body; and a concentration measurement unit for measuring the concentration of the constituent in the blood based on variation of light intensity of light received by the light receiving unit, the variation attributed to a pulse wave of the living body.

11 Claims, 7 Drawing Sheets

DEVICE FOR MEASURING CONCENTRATION OF CONSTITUENT IN BLOOD AND MEASURING METHOD

CROSS REFERENCE TO RELATED APPLICATION

This application is based on Japanese Patent Application No. 2008-115337 filed on Apr. 25, 2008, the disclosure of which is incorporated herein by reference.

FIELD OF THE INVENTION

The present invention relates to a device for measuring concentration of a constituent in blood of a living body and a method for measuring concentration of a constituent in blood.

BACKGROUND OF THE INVENTION

Conventionally, a technique for measuring concentration of constituents in blood without invasion of a living body is disclosed. For example, Patent Document No. 1 teaches the following technique. Near infrared light having at least one of wavelengths selected in a range between 780 nm and 1300 nm is irradiated on a human body. Then, an intensity of transmitted light is measured. Based on the intensity of the transmitted light, a concentration of glucose in the human body is detected.

[Patent Document No. 1]

Japanese Patent Application Publication No. H5-176917

However, in the above prior art, at the time of measurement, even when a degree of force for press-contacting a part of the body to be measured is slightly changed, a measured value may be changed. Thus, measurement with high accuracy cannot be performed.

SUMMARY OF THE INVENTION

In view of the above-described problem, it is an object of the present disclosure to provide a device for measuring concentration of constituents in blood of a living body. It is another object of the present disclosure to provide a method for measuring concentration of constituents in blood.

According to a first aspect of the present disclosure, a device for measuring concentration of a constituent in blood includes: an irradiation unit for irradiating light toward a living body, the light having a wavelength disposed in a light absorption band of the constituent in the blood; a light receiving unit for receiving light, which is reflected in the living body or transmitted through the living body; and a concentration measurement unit for measuring the concentration of the constituent in the blood based on variation of light intensity of light received by the light receiving unit, the variation attributed to a pulse wave of the living body. Thus, the device for measuring concentration of constituents in blood can measure the concentration of the constituents in the blood with high accuracy and without invasion of a living body.

According to a second aspect of the present disclosure, a method for measuring concentration of a constituent in blood include: irradiating light toward a living body, the light having a wavelength disposed in a light absorption band of the constituent in the blood; receiving light reflected in the living body or transmitted through the living body; and measuring the concentration of the constituent in the blood based on variation of light intensity of received light, the variation attributed to a pulse wave of the living body. Thus, the method for measuring concentration of constituents in blood provides to measure the concentration of the constituents in the blood with high accuracy and without invasion of a living body.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

1. Construction of Device for Measuring Concentration of Constituents in Blood

Figure 1:
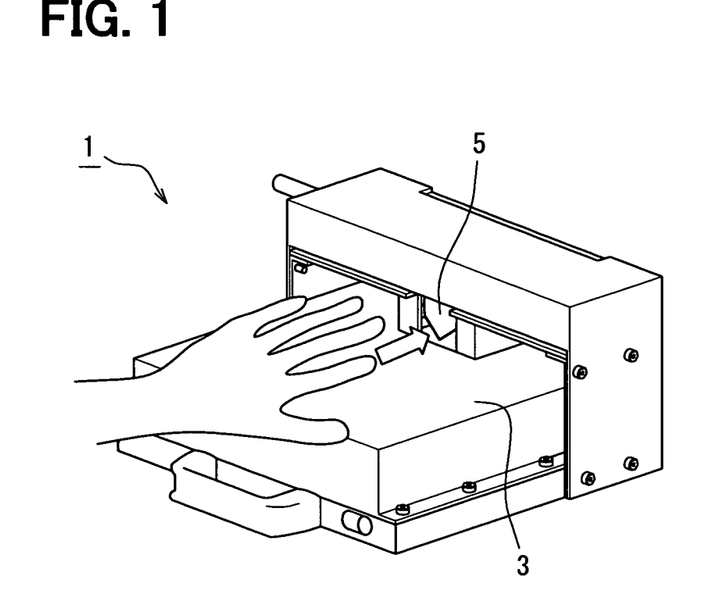
FIG. 1 is a perspective view showing a device for measuring concentration of constituents in blood.
Figure 2:
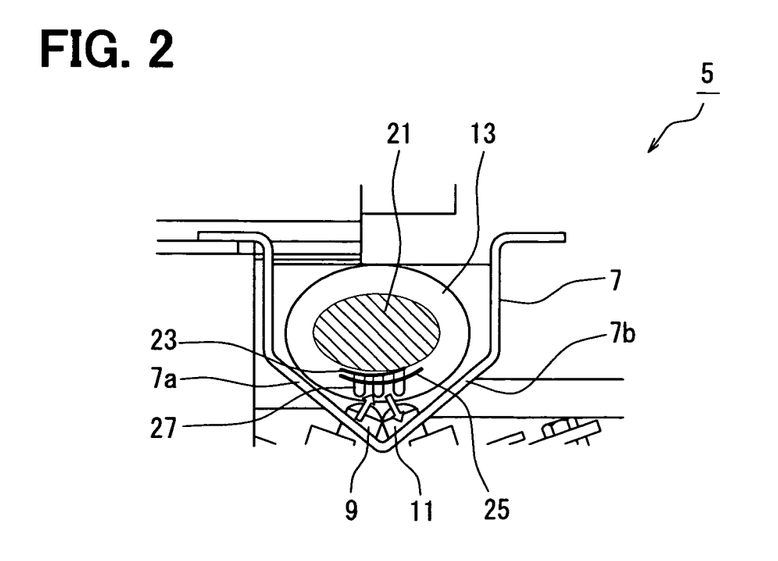
FIG. 2 is a front view showing a measurement unit.
Figure 3A:
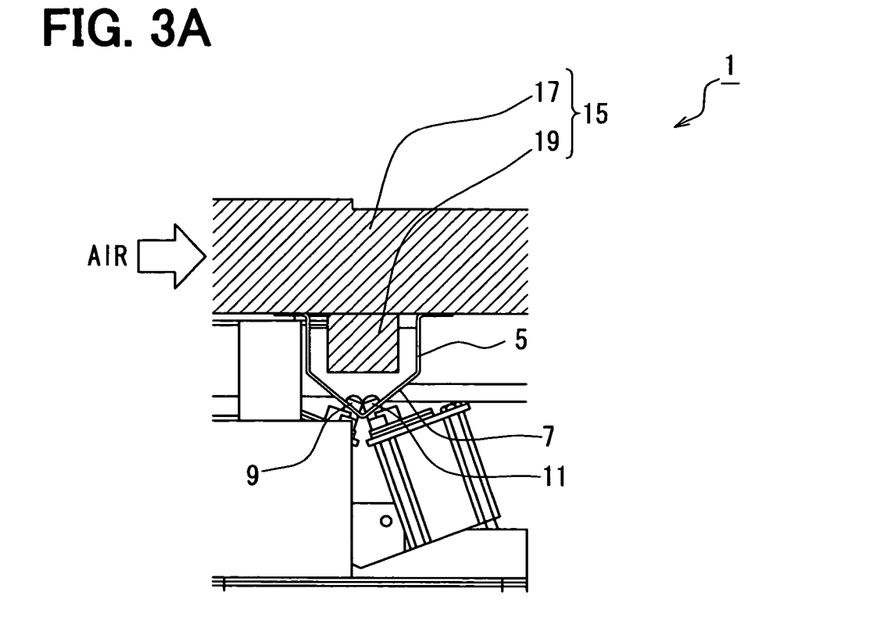
FIG. 3A is a front view showing a fingertip-holding unit under a condition that the unit presses the fingertip.
Figure 3B:
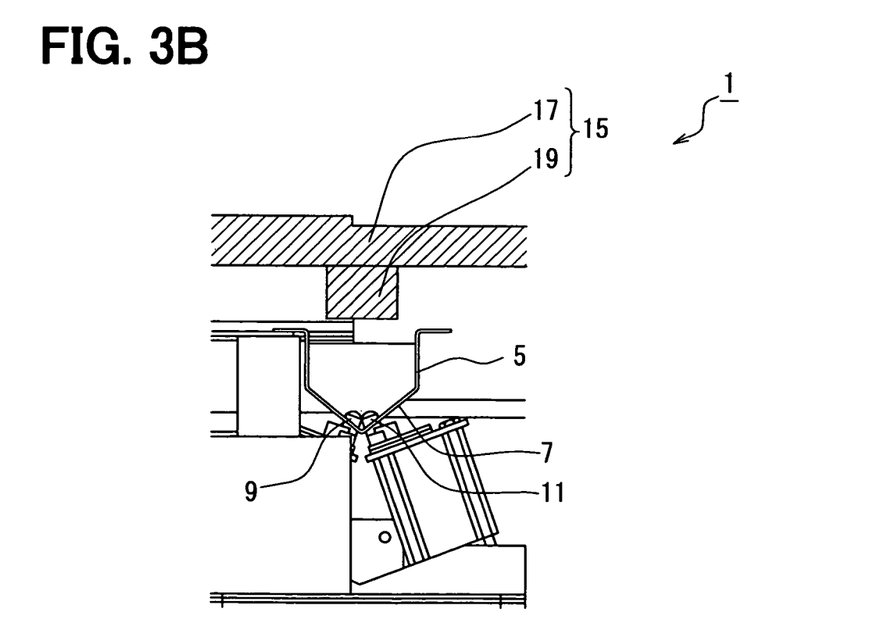
FIG. 3B is a front view showing the fingertip-holding unit under a condition that the unit releases the fingertip.
Figure 4:
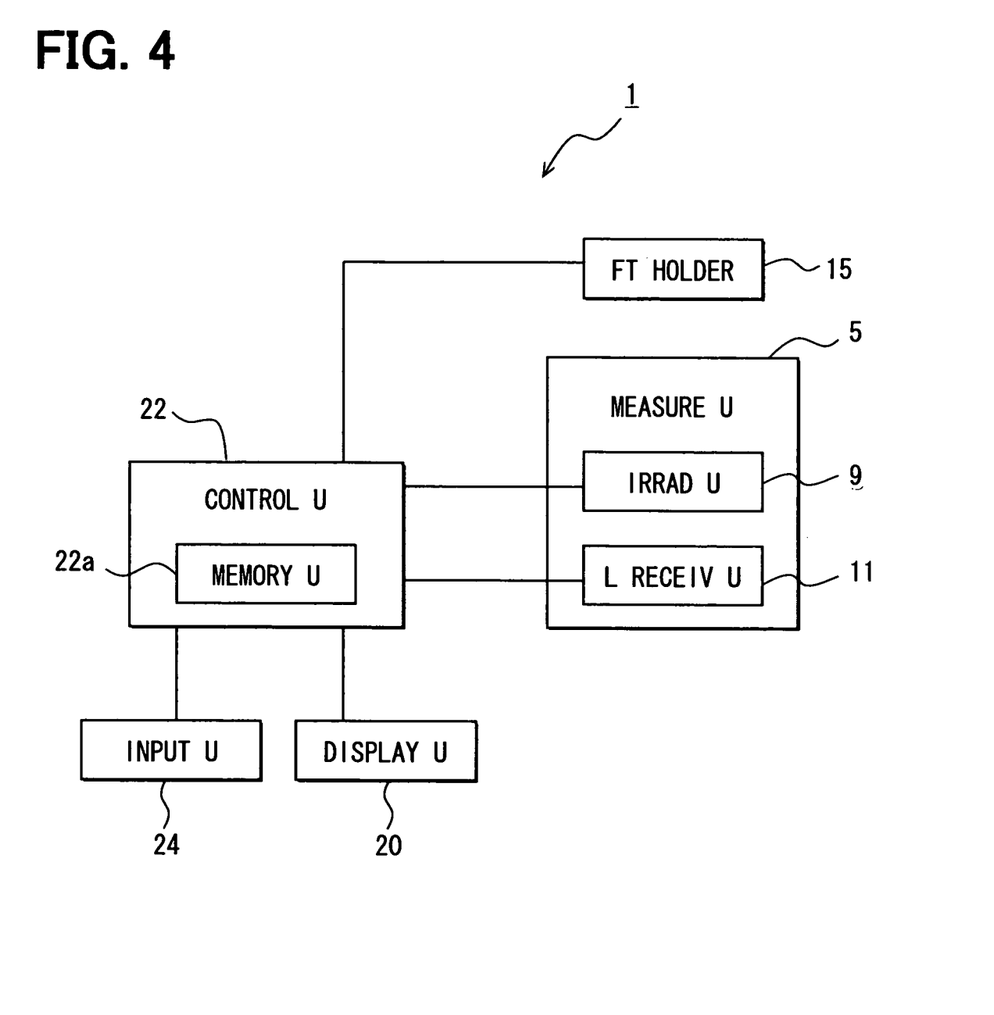
FIG. 4 is a circuit diagram showing the device for measuring concentration of constituents in blood.

A construction of a device 1 for measuring concentration of constituents in blood will be explained with reference to FIGS. 1-4. FIG. 1 is a perspective view showing a whole construction of the device 1 for measuring concentration of constituents in blood. FIG. 2 is a front view showing a measurement unit 5. FIGS. 3A and 3B are front views showing a fingertip-holding unit 15. FIG. 4 is a block diagram showing electric configuration of the device 1 for measuring concentration of constituents in blood.

As shown in FIG. 1, the device 1 for measuring concentration of constituents in blood includes a stage 3 for mounting a palm and a measurement unit 5. A palm of a trial subject (i.e., a human) can be mounted on the stage 3. A fingertip can be inserted into the measurement unit 5 under a condition that the palm is mounted on the stage 3.

As shown in FIG. 2, the measurement unit 5 includes a main body unit 7, an irradiation unit 9 and a light-receiving unit 11. The main body unit 7 is a drain having a substantially V-shaped bottom. The main body unit 7 has dimensions capable of inserting a fingertip 13 of the trial subject therein. The irradiation unit 9 is mounted on a first bottom surface 7a for providing the V-shaped bottom of the main body unit 7. The irradiation unit 9 is capable of irradiating light toward the inside of the main body unit 7. The irradiation unit 9 includes a LED as a light source so that the irradiation unit 9 irradiates light having a predetermined wavelength. Alternatively, a LD may be used for the light source. Further, light dispersed by an optical filter and a prism may be irradiated. The irradiation unit 9 may be formed with a rounded irradiation surface. The light-receiving unit 11 is mounted on a second bottom surface 7b for providing the V-shaped bottom of the main body unit 7. The light-receiving unit 11 is capable of receiving light irradiated by the irradiation unit 9. The light-receiving unit 11 may be formed with a rounded reception surface. The light-receiving unit 11 includes a conventional photo diode (i.e., PD) or a photo cell for receiving light, and converts the light to an electric signal. The irradiation unit 9 and the light-receiving unit 11 are disposed such that an optical axis of the irradiation unit 9 intersects with an optical axis of the light receiving unit 11.

The device 1 for measuring concentration of constituents in blood includes a fingertip-holding unit 15 shown in FIGS. 3A and 3B disposed over the measurement unit 5. The fingertip-holding unit 15 includes a sack unit 17 as a sac-like member and a pressing unit 19 made of sponge. The pressing unit 19 is mounted under the sack unit 17. When air is supplied to the sack unit 17 from a pressure pump not shown, the sack unit 17 inflates, as shown in FIG. 3A. At this time, the pressing unit 19 is displaced downward, so that the pressing unit 19 press-contacts from above the fingertip, which is mounted on the measurement unit 5. Thus, the pressing unit 19 presses the fingertip downward. As a result, as shown in FIG. 2, the fingertip 13 is pressed on the irradiation unit 9 and the light-receiving unit 11. Thus, a relative positional relationship among the fingertip 13, the irradiation unit 9 and the light-receiving unit 11 is maintained constant. Under these conditions, the concentration of constituents in blood is measured. The pressing pressure of the pressing unit 19 is set to be 20±5 Pa.

When the air is discharged from the sack unit 17, as shown in FIG. 3B, the sack unit 17 deflates, so that the pressing unit 19 is displaced upward. At this time, the pressing unit 19 does not contact the fingertip, which is mounted on the measurement unit 5. Thus, the fingertip is freely put in and pulled out from the measurement unit 5.

As shown in FIG. 4, the device 1 for measuring concentration of constituents in blood includes a display unit 20 formed of a liquid crystal display for displaying various information. Further, the device 1 for measuring concentration of constituents in blood includes a control unit 22 for controlling the measurement unit 5, the fingertip-holding unit 15 and the display unit 20 and for executing later described various calculation based on the electric signal obtained in the measurement unit 5. The control unit 22 includes a memory unit 22a for memorizing various data such as a reference wave height and a standard curve. The device 1 for measuring concentration of constituents in blood further includes an input unit 24 formed of a key board for inputting information into the control unit 22.

2. Measurement Method of Concentration of Constituents in Blood

Firstly, as shown in FIG. 2, the fingertip 13 of the trial subject is inserted into the measurement unit 5 of the device 1 for measuring concentration of constituents in blood. Then, the fingertip 13 is maintained at a predetermined position by using the fingertip-holding unit 15 (as shown in FIGS. 3A and 3B).

Figure 5:
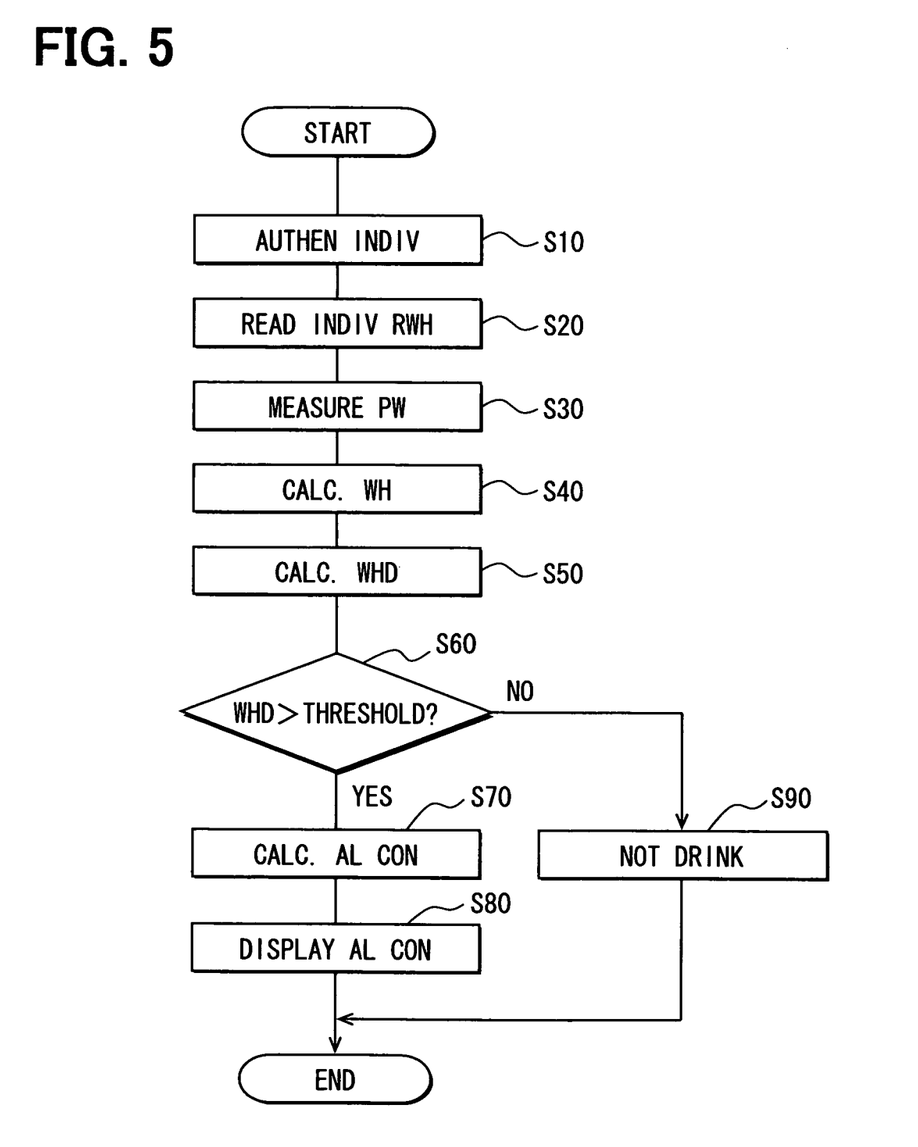
FIG. 5 is a flowchart showing a process executed by the device for measuring concentration of constituents in blood.

Under the above conditions, the device 1 for measuring concentration of constituents in blood (specifically, the control unit 22) measures the concentration of constituents in blood according to a procedure shown as a flowchart in FIG. 5. Here, alcohol as the constituent in blood is measured.

In Step S10, person authentication of the trial subject is performed, or individual other than human may be authenticated. Specifically, the person authentication is performed based on a password input in the input unit 24 (as shown in FIG. 4). Alternatively, the person authentication may be performed based on living body information such as a finger pattern and a vein pattern.

In Step S20, the reference wave height (i.e., RWH) corresponding to the trial subject is read out from the memory unit 22a (shown in FIG. 4). The reference wave height will be explained later. The reference wave height of each trial subject is preliminary stored in the memory unit 22a. The reference wave height corresponding to a person who is authenticated in Step S10 is read out.

Figure 6:
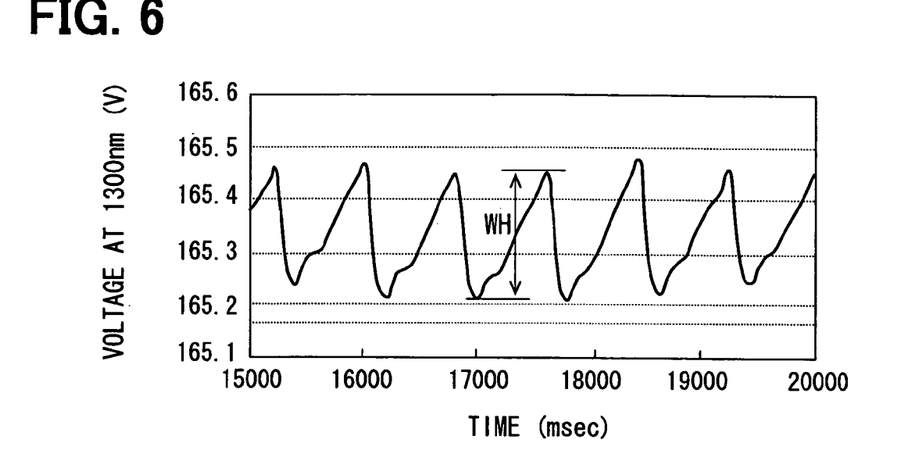
FIG. 6 is a graph showing a waveform of an electric signal corresponding to light entered into a light-receiving unit when a trial subject does not drink.
Figure 7:
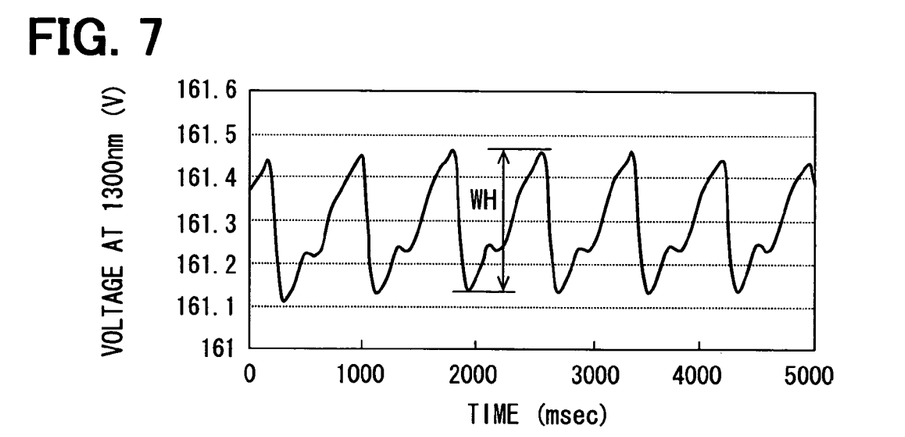
FIG. 7 is a graph showing a waveform of an electric signal corresponding to light entered into a light-receiving unit 11 when the trial subject drinks.

In Step S30, a pulse wave (i.e., PW) is measured as described below. As shown in FIG. 2, the irradiation unit 9 irradiates the light having a wavelength (of 1300 nm) toward the fingertip 13. The light is disposed in a light absorption band of alcohol. A bone 21, an artery 23, a vein 25 and a blood capillary 27 exist in the fingertip 13. The light emitted from the irradiation unit 9 penetrates in the fingertip 13. Then, the light reaches the blood capillary 27. At this time, a part of the light having a certain wavelength is absorbed in an alcohol molecule contained in blood of the blood capillary 27. Another part of the light that is not absorbed is entered in the light-receiving unit 11. The light entered in the light-receiving unit 11 is converted to an electric signal. The control unit 22 obtains the electric signal corresponding to the light entered in the light-receiving unit 11 in chronological order. As shown in FIGS. 6 and 7, the control unit 22 obtains a waveform varying periodically attributed to a pulse wave. FIG. 6 shows a waveform for a trial subject without drinking. FIG. 7 shows a waveform for a trial subject after drinking.

In Step S40, as shown in FIGS. 6 and 7, a wave height (i.e., WH and a difference between a peak and a bottom of a waveform varying periodically attributed to the pulse wave) is calculated in the waveform obtained in Step S30. Here, the reference wave height is a wave height calculated from a waveform corresponding to the trial subject who does not drink.

In Step S50, the reference wave height read out in Step S20 is subtracted from the wave height calculated in Step S40 so that a wave height difference (i.e., WHD) is calculated.

In Step S60, it is determined whether the wave height difference calculated in Step S50 is larger than a predetermined threshold (i.e., it is determined whether the wave height difference calculated in Step S50 is larger by a predetermined value than the reference wave height). When it is determined as "YES," it proceeds to Step S70. When it is determined as "NO," it proceeds to Step S90.

In Step S70, the concentration of alcohol in blood is calculated according to the following procedure. Firstly, a ratio between the wave height calculated in Step S40 and the reference wave height is calculated (i.e., a wave height ratio is calculated). The device 1 for measuring concentration of constituents in blood preliminarily memorizes the standard curve between the wave height ratio and the concentration of alcohol in blood corresponding to individual trial subject in the memory unit 22a. By applying the wave height ratio calculated above with the standard curve, the alcohol concentration in blood is calculated.

In Step S80, the alcohol concentration in blood calculated in Step S70 is displayed on the display unit 20. Then, the process ends.

When it is determined to "NO" in Step S60, it proceeds to Step S90. In Step S90, it is determined that the trial subject does not drink. Then, the process ends.

3. Advantage of Device 1 for Measuring Concentration of Constituents in Blood (i) The device 1 for measuring concentration of constituents in blood can measure the alcohol concentration in blood without invasion of a living body and with high accuracy. This advantage is derived from the following experimental results.

Figure 8:
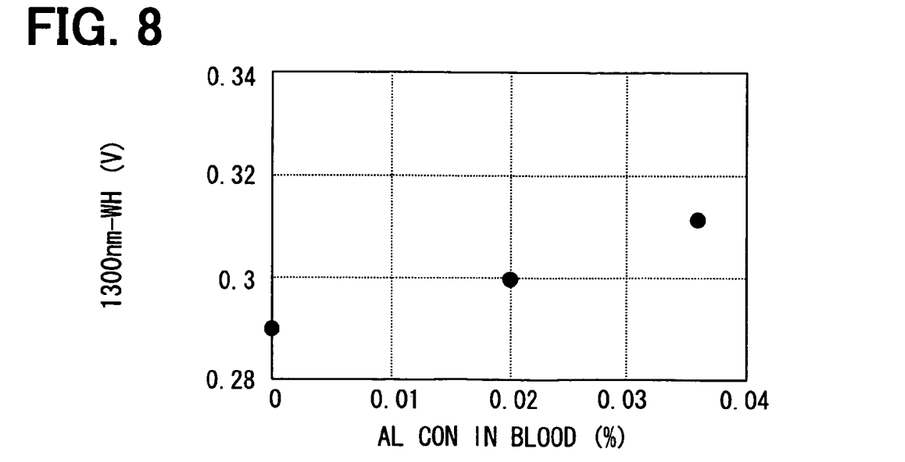
FIG. 8 is a graph showing a relationship between alcohol concentration in blood and a wave height.

The wave heights for multiple trial subjects having different alcohol concentrations in blood are calculated by the above method. Further, the alcohol concentration in blood is precisely measured by using a blood sample obtained from the same trial subjects at the same time. The relationship between the wave height and the alcohol concentration in the blood sample is shown in FIG. 8. As shown in FIG. 8, the wave height and the alcohol concentration in the blood sample are strongly correlated. Thus, it is conformed that, by using the wave height, the alcohol concentration in blood is measured with high accuracy without invasion of a living body.

The above result becomes clear by comparing the following facts. The fingertip of the trial subject is inserted into the measurement unit 5 of the device 1 for measuring concentration of constituents in blood. Then, the light (having a wavelength of 1300 nm) is emitted from the irradiation unit 9. Then, the light receiving ratio is measured at a certain time. Here, the light receiving ratio is a ratio between the intensity of light emitted from the irradiation unit 9 and the intensity of light received by the light-receiving unit 11.

Figure 9A:
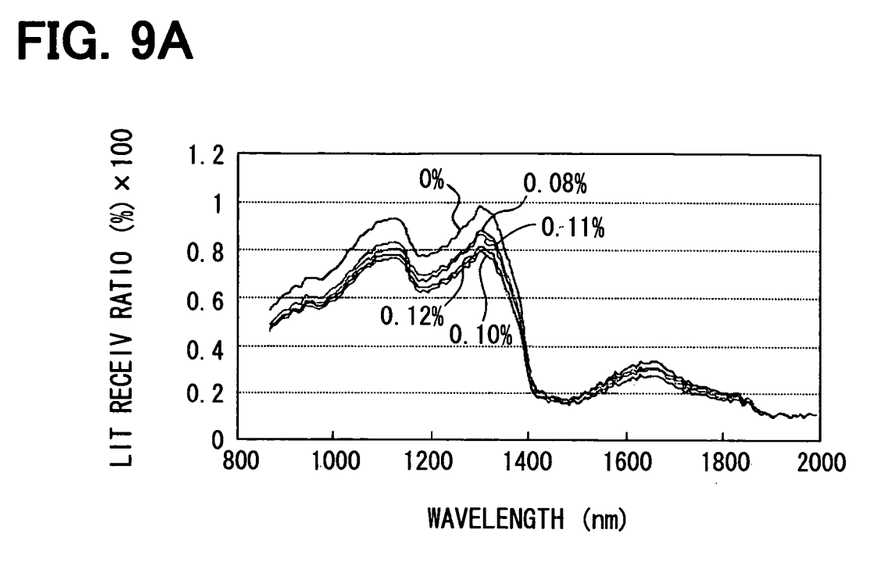
FIG. 9A is a graph showing a light receiving ratio corresponding to a drinking trial subject.
Figure 9B:
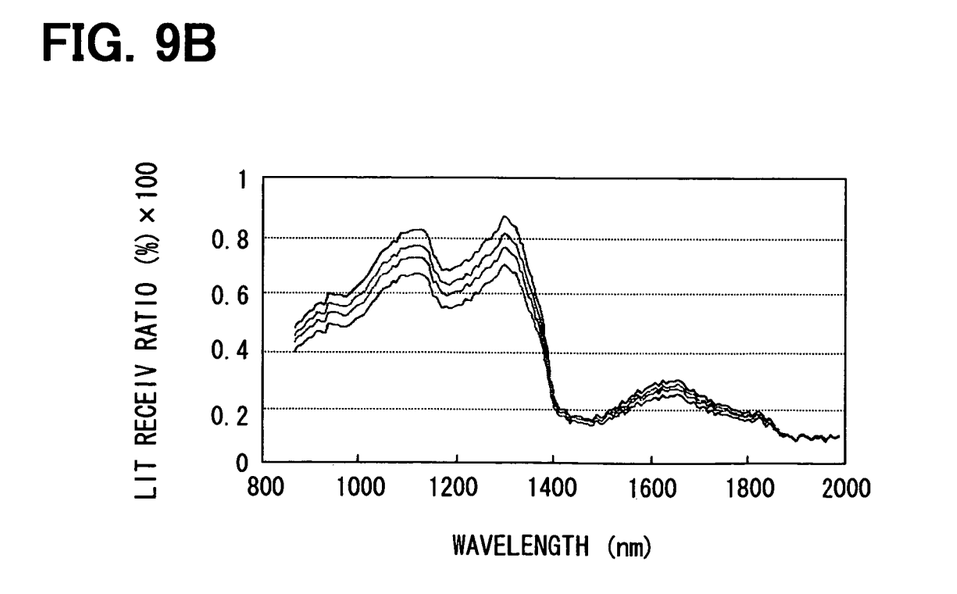
FIG. 9B is a graph showing a light receiving ratio corresponding to a not-drinking trial subject.

The light receiving ratios of multiple trial subjects having different alcohol concentrations in blood are measured, individually. The results are shown in FIG. 9A when a trial subject drinks. As shown in FIG. 9A, the light receiving ratio and the alcohol concentration in blood are not correlated at all. The light receiving ratio of the same trial subject (i.e., not drinking trial subject) is repeatedly measured. The result is shown in FIG. 9B when the same trial subject does not drink. As shown in FIG. 9B, the light receiving ratio is not reproducible, so that the value is varied in each measurement. As a result, it is difficult to measure the alcohol concentration in blood with high accuracy based on the intensity of light (i.e., the light receiving ratio) received by the light-receiving unit 11.

The reason why the alcohol concentration in blood is measured with high accuracy and without invasion of a living body when the concentration is calculated based on the wave height is supposed as follows. The blood is disposed on the outside of the blood capillary. Thus, the light emitted from the irradiation unit 9 is absorbed not only in the blood of the blood capillary but also in the blood disposed on the outside of the blood capillary. Accordingly, the light intensity received by the light is affected not only by the blood in the blood capillary but also by the blood disposed on the outside of the blood capillary. The amount and the distribution of the blood on the outside of the blood capillary are largely affected by the degree of pressing of the fingertip. As a result, the intensity of light received by the light-receiving unit 11 is largely affected by the degree of pressing of the fingertip. Accordingly, the intensity of light received by the light-receiving unit 11 is not reproducible.

On the other hand, the wave height is a height of variation attributed to the pulse wave (which is a pulsation of blood flowing in a blood vessel). Thus, the wave height is affected only by the blood in the blood capillary, not by the blood disposed on the outside of the blood capillary. Accordingly, when the alcohol concentration in blood is measured based on the wave height, the alcohol concentration is detected without being affected by the blood disposed on the outside of the blood capillary so that the concentration is measured with high accuracy and without invasion of a living body.

(ii) The device 1 for measuring concentration of constituents in blood includes the stage 3 for mounting a palm. When the alcohol concentration in blood is measured, the palm of the trial subject is mounted on the stage 3. Accordingly, during the measurement of the alcohol concentration in blood, the fingertip of the trial subject is not rotated, and thereby, the same blood capillary provides a measurement object.

(iii) The device 1 for measuring concentration of constituents in blood includes the main body unit 7 having the V-shaped bottom. When the alcohol concentration in blood is measured, the fingertip of the trial subject is held by the main body unit 7 such that the fingertip is sandwiched between the V-shaped portion. Thus, during the measurement of the alcohol concentration in blood, it is difficult to move the fingertip of the trial subject.

(iv) The pressing unit 19 presses the fingertip of the trial subject on the measurement unit 5 with an appropriate pressure. Thus, during the measurement of the alcohol concentration in blood, the fingertip is not displaced. Further, the blood capillary is not pressed excessively since the pressing force is strong.

4. Other Measurement Methods for Concentration of Constituents in Blood

Figure 10:
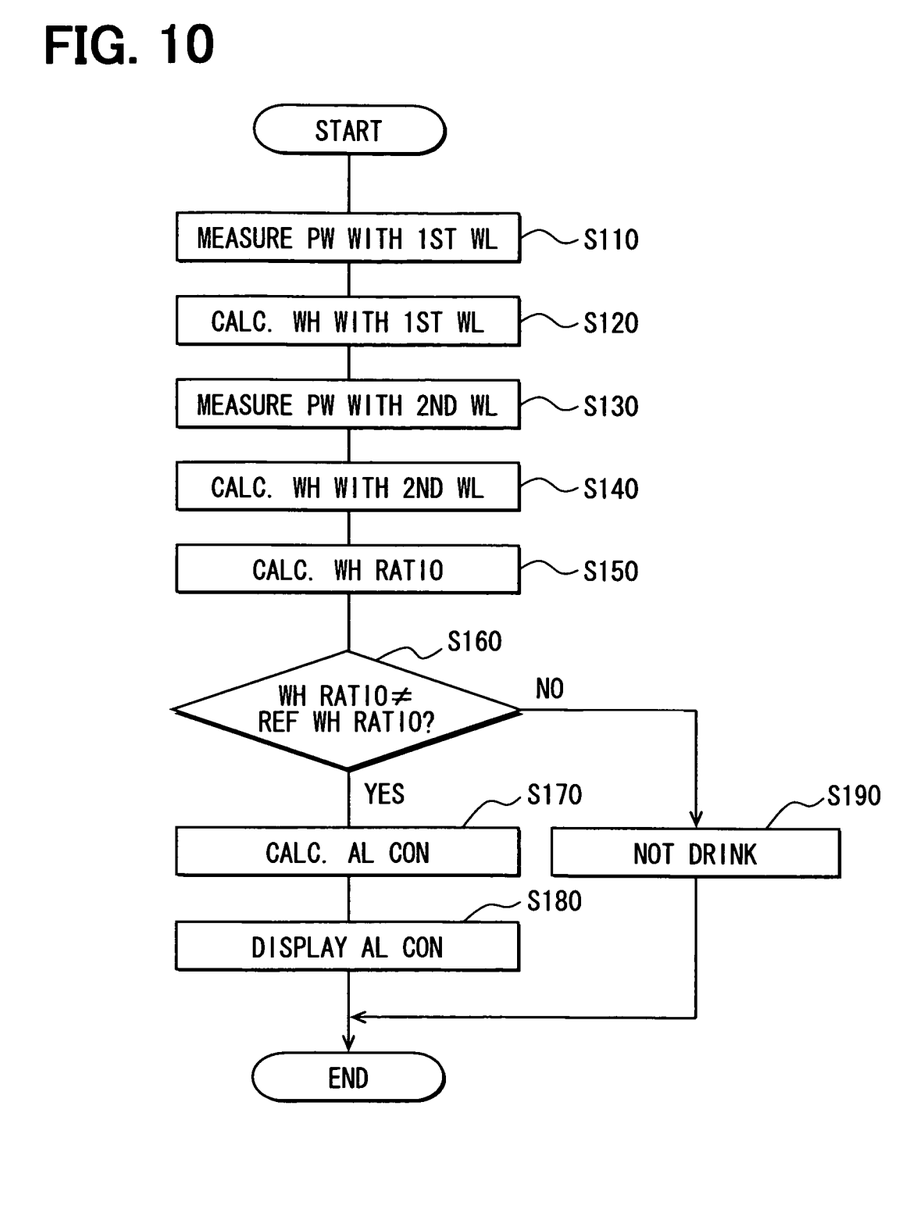
FIG. 10 is a flowchart showing another process executed by the device for measuring concentration of constituents in blood.

The device 1 for measuring concentration of constituents in blood may measure the alcohol concentration in blood with a method shown in a flowchart in FIG. 10.

In Step S10, light having a first wavelength (of 1300 nm) is used. Similar to Step S20, the pulse wave is measured.

In Step S120, the wave height is calculated in the waveform obtained in Step S10.

In Step S130, light having a second wavelength (of 1650 nm) is used. Similar to Step S20, the pulse wave is measured.

In Step S140, the wave height is calculated in the waveform obtained in Step S130.

In Step S150, a ratio between the wave height calculated in step S120 and the wave height calculated in Step S140 is calculated (i.e., a wave height ratio is calculated).

In Step S160, it is determine whether the wave height ratio calculated in Step S150 is changed from the reference wave height ratio. Here, the reference wave height ratio is a wave height ratio in a case where the alcohol concentration in blood is zero. The reference ratio is preliminarily memorized in the memory unit 22a. When it is determined that the wave height ratio is changed from the reference ratio, it proceeds to Step S170. When it is determined that the wave height ratio is not changed from the reference ratio, it proceeds to Step S190.

In Step S170, the alcohol concentration in blood is calculated. The memory unit 22a memorizes the standard curve between the wave height ratio and the alcohol concentration in blood in each trial subject. In Step S170, the wave height ratio calculated in Step S150 is applied to the standard curve, so that the alcohol concentration in blood is calculated.

In Step S180, the alcohol concentration in blood calculated in Step S170 is displayed on the display unit 20. Then, the process ends.

On the other hand, when it is determined to "NO" in Step S160, it proceeds to Step S190. In Step S190, it is determined that the trial subject does not drink. Then, the process ends.

Here, the present invention is not limited to only the above described embodiments. The present invention can be applied to various modes within a range of an aspect of the present invention.

For example, by using the device 1 for measuring concentration of constituents in blood, constituents such as glucose, glycogen, protein and cholesterol in blood other than alcohol are measured. In this case, the wavelength of light emitted from the irradiation unit 9 is adjusted according to the absorption band of each constituent in blood.

The light receiving means 11 may receive light transmitted through the fingertip.

The memory means 22a may memorize the standard curve between the wave height and the alcohol concentration in blood. The calculated wave height is applied to the standard curve so that the alcohol concentration in blood is calculated.

The above disclosure has the following aspects.

According to a first aspect of the present disclosure, a device for measuring concentration of a constituent in blood includes: an irradiation unit for irradiating light toward a living body, the light having a wavelength disposed in a light absorption band of the constituent in the blood; a light receiving unit for receiving light, which is reflected in the living body or transmitted through the living body; and a concentration measurement unit for measuring the concentration of the constituent in the blood based on variation of light intensity of light received by the light receiving unit, the variation attributed to a pulse wave of the living body.

Thus, the device for measuring concentration of constituents in blood can measure the concentration of the constituents in the blood with high accuracy and without invasion of a living body.

Alternatively, the concentration measurement unit may measure the concentration of the constituent in the blood based on variation of a wave height of light intensity attributed to the pulse wave of the living body. Further, the concentration measurement unit may measure the concentration of the constituent in the blood based on a comparison between the wave height of light intensity and a predetermined reference wave height. Here, the reference wave height is, for example, a wave height of light, which is preliminarily measured under a predetermined condition. Thus, the concentration of the constituents in the blood is measured with high accuracy and without invasion of a living body. Furthermore, the device may further includes: a memory for storing a standard curve between a wave height ratio and the concentration of the constituent in blood. The concentration measurement unit calculates the wave height ratio between the wave height of light intensity and the predetermined reference wave height, and the concentration measurement unit measures the concentration of the constituent in the blood based on the wave height ratio and the standard curve.

Alternatively, the irradiation unit may be capable of irradiating a plurality of types of light having different wavelengths. The light receiving unit is capable of receiving the plurality of types of light. The concentration measurement unit calculates the wave height of light intensity in each type of light. The concentration measurement unit measures the concentration of the constituent in the blood based on a comparison between the wave heights in different types of light. Further, the plurality of types of light may include a first light having a first wavelength and a second light having a second wavelength. The concentration measurement unit calculates a first wave height of light intensity in the first light, and calculates a second wave height of light intensity in the second light. The concentration measurement unit calculates a ratio between the first and second wave heights, and the concentration measurement unit measures the concentration of the constituent in the blood based on a comparison between the ratio and a predetermined reference ratio. Furthermore, the device may further includes: a memory for storing a standard curve between the ratio and the concentration of the constituent in blood. The concentration measurement unit measures the concentration of the constituent in the blood based on the ratio and the standard curve.

Alternatively, the irradiation unit may irradiate light toward a fingertip of the living body. Thus, the concentration of the constituents in the blood is easily measured.

Alternatively, the device may further include: a holding unit for maintaining a contact pressure of the irradiation unit to be constant, the irradiation unit press-contacting the living body. Thus, when the concentration of the constituents in the blood is measured, a measurement part of the living body is not displaced. Further, a case where a blood capillary is compressed because the contact pressure is excessively strong is avoidable.

Alternatively, the constituent in blood may be alcohol, glucose, glycogen, protein or cholesterol.

According to a second aspect of the present disclosure, a method for measuring concentration of a constituent in blood include: irradiating light toward a living body, the light having a wavelength disposed in a light absorption band of the constituent in the blood; receiving light reflected in the living body or transmitted through the living body; and measuring the concentration of the constituent in the blood based on variation of light intensity of received light, the variation attributed to a pulse wave of the living body. Thus, the method for measuring concentration of constituents in blood provides to measure the concentration of the constituents in the blood with high accuracy and without invasion of a living body.

The constituents in the blood are, for example, alcohol (e.g., ethyl alcohol), glucose, glycogen, protein, cholesterol and the like. The wavelength of light for measurement is determined according to the constituent in the blood. For example, when the constituent in the blood to be measured is alcohol, the wavelength is preferably in a range between 800 nm and 1400 nm. By using the light having the wavelength in this range, influence of individual difference of a trial subject and influence of food can be reduced, compared with a case where light having other wavelength (e.g., shorter than 800 nm). Further, when the concentration of constituents in blood is calculated based on a ratio between a value measured by using the light having the wavelength in a range between 800 nm and 1000 nm and a value measured by using the light having the wavelength in a range between 1000 nm and 1400 nm, the influence of individual difference of a trial subject and the influence of food are much reduced.

The above living body is, for example, human body or animal body.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A device for measuring concentration of a constituent in blood comprising:
    a main body unit having dimensions capable of accommodating an inserted living body;
    an irradiation unit disposed on an inner surface of the main body unit, for irradiating light toward the living body when inserted, the light having a wavelength disposed in a light absorption band of the constituent in the blood;
    a light receiving unit for receiving light, which is reflected in the living body when inserted, or transmitted through the living body when inserted; and
    a concentration measurement unit for measuring the concentration of the constituent in the blood based on variation of light intensity of light received by the light receiving unit, the variation attributed to a pulse wave of the living body when inserted, wherein the main body unit has a V-shaped bottom, wherein the irradiation unit and the light receiving unit are disposed on the V-shaped bottom, and wherein the irradiation unit has an optical axis, which intersects with an optical axis of the light receiving unit, wherein the irradiation unit has a rounded irradiation surface, wherein the light receiving unit has a rounded reception surface, and wherein the rounded irradiation surface and the rounded reception surface are each capable of contacting the living body.

2. The device according to claim 1, wherein the concentration measurement unit measures the concentration of the constituent in the blood based on variation of a wave height of light intensity attributed to the pulse wave of the living body when inserted.

3. The device according to claim 2, wherein the concentration measurement unit measures the concentration of the constituent in the blood based on a comparison between the wave height of light intensity and a predetermined reference wave height.

4. The device according to claim 3, further comprising:

a memory for storing a standard curve between a wave height ratio and the concentration of the constituent in blood, wherein the concentration measurement unit calculates the wave height ratio between the wave height of light intensity and the predetermined reference wave height, and wherein the concentration measurement unit measures the concentration of the constituent in the blood based on the wave height ratio and the standard curve.

5. The device according to claim 2, wherein the irradiation unit is capable of irradiating a plurality of types of light having different wavelengths, wherein the light receiving unit is capable of receiving the plurality of types of light, wherein the concentration measurement unit calculates the wave height of light intensity in each type of light, and wherein the concentration measurement unit measures the concentration of the constituent in the blood based on a comparison between the wave heights in different types of light.

6. The device according to claim 5, wherein the plurality of types of light includes a first light having a first wavelength and a second light having a second wavelength, wherein the concentration measurement unit calculates a first wave height of light intensity in the first light, and calculates a second wave height of light intensity in the second light, wherein the concentration measurement unit calculates a ratio between the first and second wave heights, and wherein the concentration measurement unit measures the concentration of the constituent in the blood based on a comparison between the ratio and a predetermined reference ratio.

7. The device according to claim 6, further comprising:

a memory for storing a standard curve between the ratio and the concentration of the constituent in blood, wherein the concentration measurement unit measures the concentration of the constituent in the blood based on the ratio and the standard curve.

8. The device according to claim 1, wherein the main body unit has dimensions capable of accommodating a fingertip of the inserted living body, and wherein the irradiation unit is configured to irradiate light toward the fingertip of the living body when inserted.

9. The device according to claim 1, wherein:

the irradiation unit is further configured to press-contact the living body when inserted, and the device further comprises a holding unit for maintaining a pressure at which the irradiation unit press-contacts the inserted living body when inserted.

10. The device according to claim 1, wherein the constituent in blood is alcohol, glucose, glycogen, protein or cholesterol.

11. The device according to claim 1, wherein, the wavelength of the light is in a range between 800 nm and 1400 nm.

* * * * *